(12) United States Patent
Schwartz et al.

(10) Patent No.: US 9,072,789 B2
(45) Date of Patent: *Jul. 7, 2015

(54) NANO-PARTICLE SURFACE MODIFICATION

(75) Inventors: Jeffrey Schwartz, Princeton, NJ (US); Christopher A. Traina, Napa, CA (US)

(73) Assignee: The Trustees of Princeton University, Princeton, NJ (US)

( * ) Notice: Subject to any disclaimer, the term of this patent is extended or adjusted under 35 U.S.C. 154(b) by 1351 days.

This patent is subject to a terminal disclaimer.

(21) Appl. No.: 12/176,364

(22) Filed: Jul. 19, 2008

(65) Prior Publication Data

US 2009/0028792 A1  Jan. 29, 2009

Related U.S. Application Data (60) Provisional application No. 60/951,113, filed on Jul. 20, 2007.

(51) Int. Cl.
*A61K 47/48* (2006.01)
*A61K 41/00* (2006.01)

(52) U.S. Cl.
CPC ....... *A61K 47/48084* (2013.01); *A61K 41/0057* (2013.01); *A61K 47/48861* (2013.01)

(58) Field of Classification Search
None
See application file for complete search history.

(56) References Cited

U.S. PATENT DOCUMENTS

| | | | |
|---|---|---|---|
| 2004/0023048 A1* | 2/2004 | Schwartz et al. | 428/472.1 |
| 2005/0014283 A1* | 1/2005 | Matsuura et al. | 436/166 |
| 2005/0107478 A1 | 5/2005 | Klimov et al. | |
| 2005/0206704 A1 | 9/2005 | Ikeda | |
| 2006/0194008 A1 | 8/2006 | Schwartz et al. | |
| 2006/0239913 A1 | 10/2006 | Port et al. | |

OTHER PUBLICATIONS

Samia AC, Chen X, Burda C. Semiconductor quantum dots for photodynamic therapy. 2003 J. Am. Chem. Soc. 125: 15736-15737.*
Vioux A, Le Bideau J, Mutin PH, Leclercq D. Hybrid organic-inorganic materials based on organophosphorus derivatives. 2004 Top. Curr. Chem. 232: 145-174.*
Guerrero et al. Anchoring of phosphonate and phosphinate coupling molecules on titania particles. 2001 Chem. Mater. 13: 4367-4373.*
Yang et al. Titanium dioxide nanoparticles co-doped with Fe3+ and Eu3+ ions for photocatalysis. 2002 Mater. Lett. 57: 794-801.*

* cited by examiner

*Primary Examiner* — Michael G Hartley
*Assistant Examiner* — Jennifer Lamberski
(74) *Attorney, Agent, or Firm* — Fox Rothschild LLP (57) ABSTRACT

Oxide, oxysulfide, or phosphate host particles with a self-assembled organo-phosphonate monolayer covalently bonded thereto are disclosed. Methods for coating the host particles and use of rare earth ion-doped particles in imaging methods and photodynamic therapy methods are also disclosed.

21 Claims, 3 Drawing Sheets

NANO-PARTICLE SURFACE MODIFICATION

CROSS-REFERENCE TO RELATED APPLICATION

The present application incorporates by reference and claims priority benefit under 35 U.S.C. §119(e) of U.S. Provisional Application Ser. No. 60/951,113 filed Jul. 20, 2007.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. CHE-0310178 awarded by the National Science Foundation.

FIELD OF THE INVENTION

The present invention relates to organophosphonate coated particles in general, to coated nanoparticles in particular, and to methods for coating the particles. Specifically, the present invention relates to organophosphonate particle coatings that are covalently bonded to the particle surface. The present invention also relates to coated particles in which the organo portion of the organophosphonate is selected to provide a particle with increased or decreased hydrophilicity compared to the native particle surface to stabilize particle dispersions in either polar or non-polar liquids, or to provide a surface that is functionalized for covalent bonding to a bio-molecular probe targeting reagent. The present invention also relates to organophosphonate-coated particles doped with ions of one or more rare earth elements, and to imaging methods, in vivo and in vitro assays and photodynamic therapy cancer treatment methods employing rare earth ion-doped coated particles covalently bonded to bio-molecular probe targeting ligands.

BACKGROUND OF THE INVENTION

Semiconductor quantum dots have received significant attention for biological applications such as cellular imaging, but their constituent toxic elements (e.g., CdSe) and their need for UV excitation can limit their use in vitro and compromise in vivo applications. Rare earth ion-doped nanocrystals, such as rare earth ion-doped yttrium oxide ($Y_2O_3$), are an interesting alternative to CdSe quantum dots for two significant reasons: they are nontoxic, and they can be prepared as upconversion materials. In the latter context, they absorb multiple infrared (IR) photons and emit in the visible region.

Because IR excitation is less damaging and penetrates further into living tissue than UV, upconverting nanocrystals are promising materials for in vivo imaging. However, untreated nanocrystals are not without problems: particles tend to aggregate, and they lack surface groups that can be used to attach biomolecular probes. Whereas surface coating with silica/siloxane layers is a common method of enabling particle-biomolecule conjugation, this treatment can significantly increase particle size, which affects transport to and into cells, and silica and siloxane coatings can be hydrolytically unstable under physiological conditions.

There exists a need for a nanoparticle surface treatment yielding a robust, covalently bound, hydrolytically stable organic monolayer capable of being functionalized for bonding to organic molecules that only nominally increased the particle size yet allowed the particle to be chemically bound to a biomolecular probe targeting reagent.

SUMMARY OF THE INVENTION

This need is met by the present invention. It is known that phosphonic acids can react with a variety of metal oxide surfaces to yield phosphonate monolayer films. Given the tendency of metal oxide host materials to dissolve in acidic solutions, it was unexpectedly discovered that micron-sized and nano-sized rare earth ion-doped metal oxide particles react with phosphonic acids to give stable phosphonate-coated particles.

It was further discovered that metal halides react the same way, and that metal oxysulfides and metal phosphates can also be substituted for metal oxide host particles. Through the choice of phosphonic acid structure, these particles can be directly reacted or activated for the covalent attachment of organic compounds such as biomolecular probes.

Therefore, according to one aspect of the present invention, a method is provided for coating oxide, oxysulfide, halide or phosphate particles by suspending the particles in a solution of an organophosphonic acid in a solvent until self-assembled phosphonate-bonded monolayers of the organophosphonic acid attach covalently to the particle surfaces. Mono-disperse particles less than about 100 microns in size are typically used, with particles less than about 1 micron in size being preferred. Particle size is measured by dynamic light scattering (DLS).

Oxide particles have the formula MO when M has a valence of two, $M_2O_3$ when M has a valence of three, and so forth. M is preferably a lanthanide (Ln), more preferably yttrium, wherein the oxide is represented by the formula $Ln_2O_3$. Oxysulfide particles have the formula $M_3O_2S$ when M has a valence of two, $M_2O_2S$ when M has a valence of three, and so forth. M is also preferably a lanthanide and more preferably yttrium, wherein the oxysulfide is represented by the formula $Ln_2O_2S$. Halide particles have the formula $MX_2$ when M has a valence of two, $MX_3$ when M has a valence of three, and so forth. M is preferably a lanthanide or a complex of a Group I metal and a lanthanide, and more preferably lanthanum or a sodium-yttrium complex. Lanthanide halides is represented by the formula $LnX_3$, with lanthanum halides represented as $LaX_3$. A halide salt of a lanthanide-sodium complex, for example, is represented as $NaLnX_4$, with sodium-yttrium complexes represented as $NaYX_4$. The preferred halides are fluorides.

The inventive method can be used to coat rare earth ion-doped luminescent particles. Such particles are doped prior to coating with ions of one or more rare earth elements. Examples of rare earth elements include strontium, europium, cerium, terbium, dysprosium, holmium, erbium, thulium, ytterbium and lutetium. The invention can also be used to coat particles that are not doped with rare earth ions, and which are not luminescent. Such coated particles have use in printing inks where the ability to form a stable particle suspension in a polar or non-polar solvent is critical.

When the particles are oxides or oxysulfides, the organophosphonic acid has the formula R—P(=O)(—OH)$_2$, wherein R is an organic moiety that is either more or less hydrophilic than the native particle surface, and is optionally functionalized, either to make the R group more or less hydrophilic, or for conjugation of biomolecular probe targeting reagents. When the particles are halides, the organophosphonic acid has the formula R—P(=O)(—OR$_1$)$_2$, wherein R is the same organic moiety as the R group on the organophosphonic acid used to coat the oxide and oxysulfide particles, and each $R_1$ is independently selected from —H and —Si($R_2$)$_3$, wherein each $R_2$ is independently selected from one to about six carbon atom alkyl groups. When the halide is a fluoride, it is preferred that at least one $R_1$ group be an —Si($R_2$)$_3$ group because the reaction of a phosphonic acid with fluoride particles forms undesirable quantities of hydrogen fluoride. The —Si($R_2$)$_3$ moiety reacts to sequester the HF for collection and removal from the coated particle suspension.

The organophosphonic acid layer covalently bonds to the particle surfaces by means of the —OH and —OR$_1$ groups. For purposes of the present invention the bonds are referred to as phosphonate bonds regardless of the particle composition. Through the choice of the phosphonic acid R group, the hydrophilicity of the particles may be controlled, which can be employed to form stable suspensions of the coated particles in a variety of polar and non-polar solvents.

R is selected from linear or branched alkyl or alkylenyl moieties with from about two to about 40 carbon atoms and 0 to about 20 heteroatoms preferably selected independently from oxygen and nitrogen. Preferred alkyl and alkylenyl moieties are linear or branched and have from about two to about 20 carbon atoms and 0 to about ten heteroatoms preferably selected independently from oxygen and nitrogen.

Hydrophobic R groups are used form a coating less hydrophilic than the native particle surface, while hydrophilic R groups are used to form a coating more hydrophilic than the native particle surface. Hydrophilic R groups include poly(alkylene oxide) moieties, among which polyethylene glycols are preferred. Also preferred are organic moiety R groups that are disposed to participate in a close-packing arrangement when the acid is adsorbed onto the particle surface.

The R groups may be optionally substituted with one or more functional groups selected from hydroxyl functional groups, amino functional groups, carboxylic acid functional groups, carboxylate functional groups, phosphonic acid functional groups, phosphonate functional groups, ether functional groups, alkyne functional groups, azide functional groups, thiol functional groups, and the like. The use and selection of functional groups will depend up on the extent to which the coating is intended to increase or decrease particle hydrophilicity, which can be readily determined by one of ordinary skill in the art without undue experimentation.

The functional group substituents may be selected for covalent attachment of biomolecular probe targeting reagents, in which case the functional group for biomolecular probe covalent attachment is preferably omega-substituted on the organophosphonic acid R group. When R is a poly(alkylene oxide), the omega-substituent is an ether group or a hydroxyl group, which may be activated by conventional methods to conjugate a probe molecule thereto.

According to another aspect of the present invention, coated particles prepared by the method of the present invention are provided. That is, the present invention also provides oxide, oxysulfide, halide or phosphate particles with a self-assembled organophosphonate monolayer covalently bonded thereto. The particles may be doped with rare-earth ions. However, the present invention includes particles that are not rare earth ion doped.

Through the choice of phosphonic acid structure, these particles can be made to be either more hydrophilic or less hydrophilic than the native particle surface. A more hydrophilic particle surface improves the stability of particle suspensions in polar solvents so that the particles do not sink to the bottom or float to the top of the solvent. The stability of particles encapsulated by micelles or liposomes with hydrophilic cores and hydrophobic exteriors is also improved and reduces the tendency of the particle to be ejected from the liposome or micelle. Likewise, a more hydrophobic particle surface improves the stability of particle suspensions in non-polar solvents or when encapsulated by micelles or liposomes with hydrophobic cores and hydrophilic exteriors.

Therefore, according to another aspect of the present invention, solvent suspensions of the coated particles of the present invention are provided. The particles may have a coating more hydrophilic than the native particle surface, in which case the solvent is a polar solvent. The particles with hydrophilic coatings may also be encapsulated by a micelle capable of suspending a hydrophilic particle in a hydrophobic solvent, or by a liposome or cyclodextrin with a hydrophilic core and a hydrophobic exterior, in which case the solvent is a non-polar solvent.

According to another embodiment of this aspect of the invention, the particles may have a coating more hydrophobic than the native particle surface, in which case the solvent is a non-polar solvent. The particles with hydrophobic coatings may also be encapsulated by a micelle capable of suspending a hydrophobic particle in a hydrophilic solvent, or by a liposome or a cyclodextrin with a hydrophobic core and a hydrophilic exterior, in which case the solvent is a polar solvent. According to both embodiments the solvent-particle suspensions may be formulated as printing inks in general and ink jet printing inks in particular.

The organic moiety on the organophosphonate may be substituted with functional group substituents selected for covalent attachment of biomolecular probe targeting reagents, in which case the functional group for biomolecular probe covalent attachment is preferably omega-substituted and the particles are doped with rare earth ions.

According to yet another aspect of the present invention particle-probe conjugates are provided, formed by the covalent attachment of biomolecular probes to functional groups on the organic moiety of the organophosphonate particle coating. Particle-probe combinations may be prepared, such as the combinations using rare earth ion-doped particles disclosed by Zarling et al., U.S. Pat. No. 5,698,397, the disclosure of which is incorporated by reference, with the present invention representing an improvement in the method by which the particle-probe combinations of the above-referenced patent are prepared.

Tissues can thus be imaged by conventional techniques by labeling the tissue to be imaged with the rare earth ion doped particle-probe conjugates of the present invention using a probe component that binds preferentially to biological markers on the tissue to be imaged. Visible light emission from the particles can be observed via conventional light microscopy or an image can be generated from either visible or infrared light emission from the particles using conventional imaging hardware and software.

Therefore, according to still yet another aspect of the present invention, a method is provided for tissue imaging by labeling a tissue to be imaged with the organophosphonate-coated rare earth ion-doped particles of the present invention covalently bonded to probes that bind specifically to biological markers on the tissue; exciting the particles with tissue-penetrating electromagnetic radiation of a wavelength that stimulates the rare earth ions to emit photons; and converting the photon emission to a visible image. Nanometer (nm) scale particles are preferred, with particles having a particle size capable of penetrating the blood-tissue barrier being more preferred. Tissue-penetrating radiation capable of stimulating rare-earth ions to emit photons includes x-ray and infrared wavelengths. The emitted photons may include visible and infrared wavelengths.

Depending upon location, the tissue can be imaged in-vivo via minimally invasive internal instrumentation, or by exposing the tissue to be imaged in a sterile environment to permit the image to be captured. The present invention can further be used to obtain high resolution images of ex-vivo tissue sections of biopsy samples. In addition, one of ordinary skill in the art will understand how the present invention can be applied to the analyte detection techniques of the above-referenced U.S. Pat. No. 5,698,397.

The rare earth ion-doped coated particle-probe conjugates can also be employed with photodynamic therapy (PDT) methods. PDT is a light based cancer treatment where a photosensitizing drug is activated with a visible light. PDT is executed by administering the photosensitizing drugs (which are non-toxic and inactive without light) intravenously and/or locally and illuminating them with visible light. The light energy is captured by the photosensitizing drugs, which then transfer that energy to produce toxic species, typically by transferring that energy to molecular oxygen, generating excited quantum states of oxygen that effect PDT. It is an extremely effective cancer treatment and works by several mechanisms: direct cell kill, induced cell death (apoptosis), destruction of neovascularization supplying a tumor, induction local inflammation response to tumor, systemic immune response to tumor.

The greatest limitation to employing PDT is light delivery, as the activating wavelengths of visible light only penetrate tissue for several millimeters. Until now it was not possible to treat a tumor with PDT if it was not accessible for having a light shined directly on it.

Yet another aspect of the present invention thus provides a PDT method for treating a living being in need thereof using the particle-probe conjugates of the present invention. At least one photosensitizing agent is introduced into the body of the living being in proximity to diseased tissue, wherein the photosensitizing agent generates species toxic to the diseased tissue in response to stimulation by visible or infra red light. Rare earth ion-doped coated particle-probe conjugates of the present invention in which the probe binds specifically to the diseased tissue are introduced into the body of the living being, wherein the rare earth ions in the particles are excitable by tissue-penetrating radiation to produce visible or infra-red light and the photosensitizing agent is in sufficient proximity to the particle-probe conjugate to stimulate the production of the toxic species. Tissue-penetrating radiation for exciting the luminescent compound is then applied thereto from a source that is within minimally invasive or non-invasive excitation proximity of the luminescent compound.

The foregoing and other objects, features and advantages of the present invention are more readily apparent from the detailed description of the preferred embodiments set forth below, taken in conjunction with the accompanying drawings.

DETAILED DESCRIPTION OF PREFERRED EMBODIMENTS

The subject invention provides a method by which oxide, oxysulfide, halide or phosphate particles in general, and rare earth ion-doped luminescent oxide, oxysulfide, halide or phosphate particles in particular, may be coated with self-assembled organophosphonate monolayers that covalently attach to the particle surface, whereby the particles can be made either more hydrophilic or less hydrophilic than the native particle surface. Embodiments of the present invention include covalently attached organophosphonate coatings that are functionalized and which can be activated, if necessary, for the covalent attachment of organic compounds such as biomolecular tissue targeting probes.

The present invention can be practiced with essentially any metal oxide, oxysulfide, halide or phosphate particle which may or may not be doped with a plurality of the same or different rare earth ions. Oxide particles have the formula MO when M has a valence of two, $M_2O_3$ when M has a valence of three, and so forth. Oxysulfide particles have the formula $M_3O_2S$ or $M_3OS_2$ when M has a valence of two, $M_2O_2S$ or $M_2OS_2$ when M has a valence of three, and so forth. Halide particles have the formula $MX_2$ when M has a valence of two, $MX_3$ when M has a valence of three, and so forth. M is preferably a lanthanide and more preferably is yttrium when the particle is an oxide or oxysulfide and lanthanum when the particle is a halide.

Particles can optionally be doped prior to coating with any rare earth element or combinations thereof (i.e., europium, cerium, terbium, dysprosium, holmium, erbium, thulium, ytterbium, lutetium, etc.) with europium, cerium, terbium, holmium, erbium, thulium and ytterbium being preferred, and the following combinations also being preferred: ytterbium and erbium, ytterbium and holmium and ytterbium and thulium. Strontium can also be used, and for purposes of the present invention, rare earth elements are defined as including strontium. M can be, but is not limited to, lanthanum, yttrium, lead, zinc, cadmium, and any of the Group II metals such as, berylium, magnesium, calcium, strontium, barium, aluminum, radium and any mixtures thereof or a metalloid selected from silicon, germanium and II-IV semi-conductor compounds.

One type of luminescent particle host material generally has the structure $L_2O_3$, wherein L represents one or more rare earth elements of the lanthanide series. Luminescent materials suitable for use in the invention may contain a plurality of $L_2O_3$ compounds. Examples of suitable phosphor host materials include sodium yttrium fluoride ($NaYF_4$), yttrium oxide ($Y_2O_3$), lanthanum fluoride ($LaF_3$), lanthanum oxysulfide ($La_2O_2S$), yttrium oxysulfide ($Y_2O_2S$), yttrium fluoride ($YF_3$), gadolinium fluoride ($GdF_3$), barium yttrium fluoride ($BaYF_5$, $BaY_2F_8$), calcium tungstate ($CaWO_4$) and gadolinium oxysulfide ($Gd_2O_2S$).

Examples of rare earth ion-doped luminescent particles suitable for use in the present invention are described in U.S. patent application Ser. No. 11/494,157, the disclosure of which is incorporated by reference. Specific examples of luminescent materials include Yttrium Oxide:Terbium ($Y_2O_3$:Tb), Gadolinium Oxysulfide:Europium ($Gd_2O_2S$: Eu); Lanthanam Oxysulfide:Europium ($La_2O_2S$:Eu); and Gadolinium Oxysulfide:Promethium, Cerium, Fluorine. Other infra red excitable luminescent materials are disclosed in this application including rare earth ion-doped $Er_2O_3$ and $Y_2O_3$.

Two rare earth element ions may be paired as activator couples to tailor particle performance to specific absorption and emission wavelengths. For example ytterbium and erbium act as an activator couple in a phosphor host material such as barium-yttrium-fluoride. The ytterbium ions act as absorber, and transfers energy non-radiatively to excite the erbium ions. The emission is thus characteristic of the erbium ion's energy levels.

Suitable activator couples are selected from: ytterbium/erbium, ytterbium/thulium, and ytterbium/holmium. Other activator couples suitable for up-conversion may be used. By combination of the host materials with the activator couples, at least three phosphors with at least three different emission spectra (red, green, and blue visible light) are provided. Typically the absorber is ytterbium and the emitting center is selected from: erbium, holmium, terbium, and thulium; however, up-converting phosphors of the invention may contain other absorbers and/or emitters.

Examples of other suitable oxide, oxysulfide and halide phosphor particles and the methods by which they are made are described by Riman et al., U.S. Pat. No. 6,699,406, Kane, U.S. Pat. No. 5,891,361, Ohwaki et al., U.S. Pat. No. 5,541,012 and Austin et al., U.S. Patent Application Publication No. US-2006-0269483-A1. The disclosures of all three patents and the published application are incorporated herein by reference.

The particles can also be formed by a high temperature combustion synthesis technique, such as is disclosed by Ju et al., U.S. Patent Application Publication No. 2007-0069180-A1 and U.S. patent application Ser. No. 11/537,159, the disclosures of both of which are incorporated herein by reference. Other processes for forming exemplary luminescent materials include sol-gel processes; aerogel processes; xerogel processes; co-precipitation; solution processes; spray pyrolysis processes; spray flame pyrolysis processes; chemical vapor synthesis processes; emulsion liquid membrane methods; and hydrothermal processes. Such processes can also be use to form particles that are not doped with rare earth ions.

The particles are then coated with an organophosphonate self-assembled monolayer covalently bonded to the particle surface by suspending the particles in an organophosphonic acid solution in a solvent until self-assembled phosphonate-bonded monolayers of the organophosphonic acid attach covalently to the particle surfaces. A solvent in which the organophosphonic acid is soluble should be used. The choice of solvent will depend upon the organophosphonic acid selected, which will vary in hydrophilicity depending upon whether the objective of the coating is to make the particle more or less hydrophilic than the native particle surface. The polarity of the solvent selected will increase with organophosphonate hydrophilicity, and vice versa.

Polar solvents used in the preparation of hydrophilic organophosphonic acid solutions include water, methanol, ethanol, isopropanol, n-propanol, n-butanol, hexanol, ethylene glycol, ethyl acetate, tetrahydrofuran (THF) and combinations thereof. Non-polar solvents used in the preparation of hydrophobic organophosphonic acid solutions include carbon tetrachloride, methylene chloride, toluene, chloroform, and combinations thereof. Both hydrophilic and hydrophobic organophosphonic acids are soluble in certain solvents such as ethyl acetate, THF, ethanol, methanol, and combinations thereof. Solution concentrations range between about 0.1 vol. % and about 80 vol. %, and preferably between about 1 vol. % and about 50 vol. %.

The particles are suspended in the organophosphonic acid solution by conventional means, such as physical stirring or sonication. Between about 0.1 and about 90 wt. % of particles, and preferably between about 5 and about 60 wt. %, are added to the organophosphonate solution. The suspension step is performed for at least 0.5 hours and preferably between about two and about 24 hours. The reaction proceeds under ambient conditions; however temperatures between about 0° C. and the boiling point of the solvent can be used.

Some oxide particles, such as yttrium oxide, form carbonates under ambient conditions that are preferably removed by pre-treatment of the particles with trifluoracetic acid alone or diluted to between about 0.1 and about 25 vol. % with a solvent such as, for example, acetonitrile. The particles are then washed with deionized water prior to suspension in the organophosphonic acid solution.

When the particles are oxides or oxysulfides, the organophosphonic acid has the formula R—P(=O)(—OH)$_2$, wherein R is an organic moiety that is either more or less hydrophilic than the native particle surface, and is optionally functionalized either to make the R group more or less hydrophilic, or for conjugation of biomolecular probe targeting reagents. When the particles are halides, the organophosphonic acid has the formula R—P(=O)(—OR$_1$)$_2$, wherein R is the same organic moiety as the R group on the organophosphonic acid used to coat the oxide and oxysulfide particles, and each R$_1$ is independently selected from —H and —Si(R$_2$)$_3$ wherein R$_2$ is selected from one to about six carbon atom alkyl groups.

When the halide is a fluoride, it is preferred that at least one R$_1$ group be an —Si(R$_2$)$_3$ group because the reaction of a phosphonic acid with fluoride particles forms undesirable quantities of hydrogen fluoride. The —Si(R$_2$)$_3$ moiety reacts to sequester the HF for collection and removal from the coated particle suspension R is selected from linear or branched alkyl or alkylenyl moieties with from about two to about 40 carbon atoms and 0 to about 20 heteroatoms preferably selected independently from oxygen and nitrogen. Preferred alkyl and alkylenyl moieties are linear or branched and have from about two to about 20 carbon atoms and 0 to about ten heteroatoms preferably selected independently from oxygen and nitrogen.

Hydrophobic R groups are used to form a coating less hydrophilic than the native particle surface, while hydrophilic R groups are used to form a coating more hydrophilic than the native particle surface. When R is a hydrophobic group, for example an alkyl or alkylenyl with about two to about 40 carbon atoms and less than about four oxygen or nitrogen atoms, the coated particle is more hydrophobic than the native particle surface. Examples of hydrophobic R groups include butyl, hexyl, octyl, dodecyl, octadecyl and undecyl groups, and the like.

When R is a hydrophilic group, for example, a saturated or unsaturated alkyl or alkylenyl groups with about two to about 40 carbon atoms and either one or more hydrogen bonding functional groups or from about three to about 20 heteroatoms preferably selected from oxygen or nitrogen atoms, the coated particle is more hydrophilic than the native particle surface. Examples of hydrophilic R groups include R groups substituted with one or more hydrogen bonding functional groups including polyols or sugars, carboxyls, carboxylates, amines, hydroxyls, alkoxys, and tetraorganoammonium groups, and R groups that are poly(alkylene oxide) moieties, among which polyethylene glycols are preferred and tetra-ethylene glycols are even more preferred.

Also preferred are organic moiety R groups that are disposed to participate in a close-packing arrangement when the acid is adsorbed onto the particle surface.

The R groups may be optionally substituted with one or more functional groups selected from hydroxyl functional groups, amino functional groups, carboxylic acid functional groups, carboxylate functional groups, phosphonic acid functional groups, phosphonate functional groups, ether functional groups, polyether functional groups and thiol functional groups. The use and selection of functional groups will depend up on the extent to which the coating is intended to increase or decrease particle hydrophilicity, which can be readily determined by one of ordinary skill in the art without undue experimentation.

The functional group substituents may be selected for covalent attachment of biomolecular probe targeting reagents to rare earth ion-doped particles, in which case the functional group for biomolecular probe covalent attachment is preferably omega-substituted on the organophosphonic acid R group. When R is a poly(alkylene oxide), the omega-substituent is an ether or a hydroxyl group, which may be activated by conventional methods to conjugate a probe molecule.

After the particles are coated, the suspended particles are separated from the organophosphonic acid solution by centrifuging according to conventional means. A polar solvent such as methanol may be added to help precipitate the particles on centrifugation, after which the supernatant solvents are decanted and the particles recovered for subsequent washing. The particles are washed by manual shaking in methanol to which a weak solution of NaOH (0.01 to 0.1 M) in methanol has been added. The particles are collected again by centrifugation and dried.

The reaction yields particles coated with organophosphonic acid self-assembled monolayers covalently bonded to the particle surface. The particles may be used as is for essentially any end use for a micron- or nano-sized particle that would benefit from modification of the hydrophilicity of the native surface of the particle. Examples of such end-uses include ink jet printer inks, particularly inks used for authentication purposes and for the printing of microcircuits, or essentially any end-use in which a hydrophilic or hydrophobic product is needed for a stable dispersion or suspension in a particular solvent to be formed, or to encapsulate stably in a micelle, cyclodextrin or liposome, so that particles do not float to the top of or settle to the bottom of bulk quantities of the solvent for the dispersion or suspension, or so that the particle is not ejected from the micelle, cyclodextrin or liposome.

Micelle, cyclodextrin and liposome-encapsulation processes are essentially conventional. Particles with coatings more hydrophobic than the native particle surface may be encapsulated by a micelle capable of suspending a hydrophobic particle in a hydrophilic medium. Such particles may also be encapsulated by a cyclodextrin or liposome with a hydrophobic core and a hydrophilic exterior for suspension in a hydrophilic medium. Particles with coatings less hydrophobic than the native particle surface may be encapsulated by a micelle capable of suspending a hydrophilic particle in a hydrophobic medium. Such particles may also be encapsulated by a cyclodextrin or liposome with a hydrophilic core and a hydrophobic exterior for suspension in a hydrophobic medium.

The organophosphonic acid coated rare earth ion-doped particles of the invention with omega-functionalized organic moieties can be attached to one or more probe(s) that bind specifically to biological markers in tissues to serve as a reporter (i.e., a label or detectable marker) of the location of the probe(s). The coated up-converting particles can be attached to various probes, such as anti-bodies, streptavidin, protein A, polypeptide ligands of cellular receptors, polynucleotide probes, drugs, antigens, toxins, and others. Attachment of the coated particle label to the probe can be accomplished using various linkage chemistries, depending upon the nature of the specific probe, and made possible by the omega-functionalized organic moieties on the organophosphonic acid coatings on the particle surfaces.

A preferred attachment method adapts the method described by Tanke et al., U.S. Pat. No. 5,043,265, the disclosure of which is incorporated by reference. Heterobifunctional cross-linkers are employed that can be made to link a biomolecular probe to coated particles in three steps: (1) bind the cross-linker to the omega-functionalized organophosphonate coating on the phosphor, (2) separate the unbound cross-linker from the coated particles, and (3) bind the biomolecular probe the washed, linked coated particle. This method prevents undesirable cross-linking interactions between biomolecular probes and reduces irreversible aggregation as described by the Tanke et al. patent. Examples of suitable heterobifunctional cross-linkers, omega-functionalities, and linkable biomolecular probes include, but are not limited to:

| Coating Functionality | Biomolecular Crosslinker | Heterobifunctional Probe |
|---|---|---|
| carboxylate | N-hydroxysuccimide | Proteins (e.g., Ab, avidin) |
| primary amine | 1-ethyl-3-(3-dimethyl-amino-propyl)carbodiimide (EDCI) N-5-azido-2-nitrobenzoyl oxysuccimide (ANB-NOS) N-succinimidyl (4-iodoacetyl) aminobenzoate (SIAB) | All having 1° amine |
| thiol(reduced sulfonate) | N-succinimidyl (4-iodoacetyl) aminobenzoate (SIAB) | Proteins |

One embodiment of the present invention provides organophosphonate-coated particles in which the organic moiety of the organophosphonate is a poly(alkylene oxide), such as tetra-ethylene glycol. Bifunctional poly(alkylene oxide) hydrazides and dihydrazides for linking two compounds having free carboxylic acid groups and methods of attachment are disclosed in Kohn et al., U.S. Pat. App. Publication No. 2005-0118227-A1, the disclosure of which is incorporated herein by reference. The method disclosed therein can be readily adapted to conjugate organophosphonates with poly (alkylene oxide) organic moieties to biomolecular probes with free carboxylic acid groups.

Otherwise the conjugation of poly(alkylene oxides) to biologically relevant peptides and polypeptides is routine and disclosed in Davis et al., U.S. Pat. No. 4,179,377, the disclosure of which is incorporated by reference. Zalipsky et al., U.S. Pat. No. 5,455,027 discusses prior art subsequent to Davis et al. on this subject. The disclosure of Zalipsky et al. and the relevant prior art cited therein is incorporated herein by reference. The art of conjugating poly(alkylene oxides) to peptides, polypeptides and other relevant active molecules is well known and referred to as PEGylation. Techniques known to those of ordinary skill in the PEGylation art can be used to conjugate organophosphonates with poly(alkylene oxide) organic moieties to biomolecular probes with free carboxylic acid groups.

One requirement of PEGylation is that for the reactive moiety on the active molecule to be considered available for conjugation it must not contribute to the molecular activity so that PEGylation does not inactivate the active molecule. Likewise the poly(alkylene oxide)-phosphonate coated particles of the present invention must not be conjugated to sites on bio-molecular probes that would prevent binding of the probes to the probe target. Methods by which such sites may be protected from conjugation and the conjugation directed to an inert site are well known to those of ordinary skill in the art of PEGylation.

Omega-hydroxyl organophosphonate coatings, including coatings in which the organic moiety is a poly(alkylene oxide) can also be derivatized or activated with an acid chloride or chloroformate, $R_3$—C(=O)—Cl or $R_3$—O—C(=O)—Cl, respectively. The $R_3$ group can be a linear or branched alkyl or alkylenyl group, or an aryl or alkylaryl group. The $R_3$ group can be omega functionalized like the organic moiety or ring substituted with one of the above listed functional groups other than a hydroxyl group to replace the omega-hydroxyl group with a different omega-functionality. One of ordinary skill in the art will recognize other functional groups capable of reacting with acid chlorides and chloroformates in this manner.

Other methods by which carboxylic acid functionalized polymers are conjugated to functional groups of active molecules are described in the above-referenced Zalipsky et al. patent. Detailed chemical procedures for the attachment of various drugs and ligands to polymer bound free carboxylic acid groups have otherwise been described in the literature. See, for example, U.S. Pat. Nos. 5,219,564 and 5,660,822; Nathan et al, Bio. Cong. Chem., 4, 54-62 (1993) and Nathan, Macromol., 25, 44-76 (1992). The disclosures of both patents and both journal articles are incorporated herein by reference. These publications disclose procedures by which polymers having pendent free carboxylic acid group are reacted with moieties having reactive functional groups, or that are derivatized to contain active functional groups to form a polymer conjugate. The methods disclosed therein can also be readily adapted to conjugate organophosphonates with poly(alkylene oxide) organic moieties to bio-molecular probes with free carboxylic acid groups.

The particle-probe conjugates of the present invention are useful for medical diagnostic imaging. In one embodiment, particles coupled to probes that bind to biological markers are made to emit visible or IR radiation when excited with x-ray or IR radiation, so that a patient can be irradiated with x-ray or IR radiation after the particle-probe conjugate is administered systemically or locally, and tissues with the biological marker to which the particles bind are detected with IR or visible light detection equipment.

Imaging methods with which the rare earth ion-doped probe-particle conjugates of the present invention may be used are disclosed in the above-referenced Austin et al., U.S. Patent Application Publication No. US-2006-0269483 and in PCT/U.S.07/71717 filed Jun. 21, 2007, the disclosures of which is incorporated herein by reference. The Austin et al. publication also discloses methods by which the plurality of wavelengths within the spectrum emitted by a particle can be used to assay two or more properties of tissue to which the probe binds with a single excitation wavelength.

The rare earth ion-doped probe-particle combinations of the present invention can be substituted for and are intended to replace the probe-particle combinations disclosed in these patent applications. The probe-particle combinations of the present invention can be substituted for and are intended to replace essentially any prior art probe-reporter combination, regardless of whether the reporter is organic or inorganic, and regardless of whether the probe-reporter combination is used for imaging or to assay an analyte in vivo or in vitro. Probe-reporter uses include, but are not limited to, all uses of the probe-reporter combinations disclosed by, discussed as background art in and of record in the Austin et al. publication and in PCT/U.S.07/71717, all of which are incorporated herein by reference, and all uses of the probe-reporter combinations disclosed by, of record in and discussed as background art in the above-referenced Tanke et al., U.S. Pat. No. 5,043,265 and Zarling et al., U.S. Pat. No. 5,698,397, as well as all probe-reporter uses disclosed by, of record in and discussed as background art in all patents and applications from which Zarling et al. claim priority, all patents and pending applications claiming priority to Zarling et al., and all patents and applications otherwise related to Zarling et al. All of the above-referenced patents and applications are incorporated herein by reference.

The rare earth ion-doped probe-particle combinations of the present invention are also useful in photodynamic therapy (PDT) treatment methods in which a compound or particle that upon excitation by tissue-penetrating wavelengths emits wavelengths that stimulate a photosensitizer compound co-administered therewith to produce a toxin for treatment of diseased tissue to which the probe-particle combination is targeted and binds. Such methods are described in the above-referenced PCT/U.S.07/71717. The rare earth ion-doped probe-particle combinations of the present invention can be substituted for and are intended to replace the probe-particle combinations disclosed as useful for photodynamic therapy in the PCT/U.S.07/71717. The rare earth ion-doped probe-particle combinations of the present invention can also be substituted for and are intended to replace the probe-reporter combination disclosed as being useful for PDT in the above-referenced Zarling et al. patents and applications.

In imaging, in vivo assaying and photodynamic therapy embodiments requiring injection, the particles are rare earth ion-doped, preferably monodisperse, and less than 150 nm in size to preclude capillary obstruction. The particles are more preferably monodisperse and less than 100 nm in size, and even more preferably of a monodisperse size capable of passing the blood-tissue barrier. In other delivery embodiments where the luminescent material is applied, for example by aerosolization or direct application to the chest cavity, larger particles can be used. Particle size is measured by Dynamic Light Scattering (DLS).

Imaging, in vivo assaying and photodynamic therapy compositions containing the rare earth ion-doped particle-probe combinations of the present invention, which may optionally include a photo-sensitizer dye in photodynamic therapy products, may be presented in forms permitting administration by the most suitable route. The invention also relates to administering such compositions to a patient in need thereof. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of solutions or suspensions than can be injected or administered to a treatment site following exposure of the treatment site via surgical means, for example.

The choice of vehicle and the rare earth ion-doped particle-probe combination in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used.

For parenteral administration, emulsions, suspensions or solutions of the particle-probe combinations in vegetable oil, for example sesame oil, groundnut oil or olive oil, or aqueous-organic solutions such as water and propylene glycol, injectable organic esters such as ethyl oleate, as well as sterile aqueous solutions of the particle-probe combinations, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Dispersion can also be prepared in glycerol, liquid polyethylene glycols, and mixtures thereof and in oils.

Sterile injectable solutions are prepared by incorporating the particle-probe combinations, with an optional amount of a photosensitizer dye for PDT compositions, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

Compositions for photodynamic therapy may also be prepared using the coated particles of the present invention without a probe covalently bonded thereto for methods in which the luminescent compound is applied directly to the diseased tissue without using a biomolecular probe targeting ligand. The coatings improve the stability of the particles within the formulation to be administered.

Although the present invention has been described in some detail by way of illustration for purposes of clarity of understanding, it will be apparent that certain changes and modifications may be practiced within the scope of the claims. The broad scope of this invention is best understood with reference to the following examples, which are not intended to limit the invention in any manner.

EXAMPLES

Example 1

Preparation of Acetoxy(tetra[ethyleneoxy])propyl Dimethyl Phosphonate

Dimethyl phosphite (2.481 g, 0.0226 mol) and acetoxy (tetra[ethyleneoxy]) monoallyl ether (2.095 g, 0.0076 mol) were added to a 50 mL three-necked flask fitted with a reflux condenser, an argon inlet, and a septum. The stirred solution was heated to 105° C. Tert-Butyl peroxybenzoate (0.1 mL, $5.26 \times 10^{-4}$ mol) was added via syringe to initiate the radical addition. An additional portion of radical initiator was added after 1 h and again after 2 h of reaction time. After 4.5 h of total reaction time, the mixture was allowed to cool. The resulting oil was purified by silica column chromatography using increasing amounts (0-6%) of methanol in ethyl acetate to obtain a colorless oil (0.750 g, 25% yield).

$^1$H NMR (300 MHz, CDCl$_3$, δ): 4.21 (dd, J) 3.9, 5.4 Hz, 2H), 3.74 (d, J) 10.7 Hz, 6H), 3.72-3.56 (m, 14H), 3.51 (t, J) 6 Hz, 2H), 2.06 (s, 3H), 1.92-1.76 (m, 4H). 13CNMR (100 MHz, CDCl$_3$, δ): 171.16, 70.86, 70.72, 70.67, 70.21, 69.22, 63.71, 52.42 (d, J) 6 Hz), 22.77 (d, J) 5 Hz), 21.37 (d, J) 141 Hz), 21.09. 31P NMR (121.6 Hz, CDCl3 δ): 36.21. FTIR (neat): 3461, 2952, 2870, 1738, 1456, 1375, 1352, 1246, 1182, 1113, 1055, 1031, 952, 843, 810 cm-1. LRMS (EI): 387 (M+H)

Examples 2-3

Preparation of Octadecyldimethylphosphphonate and Undecyldimethylphosphonate

Example 1 was repeated using stoichiometric amounts of 1-octadecene and 1-undecene for acetoxy(tetra[ethyleneoxy])monoallyl ether. The title compounds were obtained.

Example 4

Figure 4:
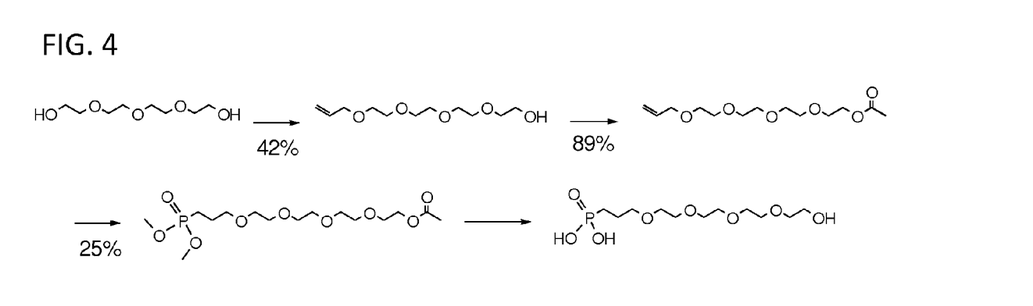
FIG. 4 depicts the scheme for the synthesis of hydroxy (tetra[ethylene-oxy])propylphosphonic acid.

Preparation of Hydroxyl(tetra[ethyleneoxy])propylphosphonic Acid (FIG. 4)

A solution of the dimethyl phosphate of Example 1 (0.271 g, $7.01 \times 10^{-4}$ mol) in 15 mL of CH$_2$Cl$_2$ was added to a 50 mL three-necked flask equipped with a stir bar, an argon inlet, and a septum. The solution was stirred at room temperature under argon, and trimethylsilyl bromide (0.5 mL, $3.7901 \times 10^{-3}$ mol) was added dropwise via syringe. The reaction mixture was stirred for 24 h. Methanol (0.109 g, $3.4001 \times 10^{-3}$ mol) was then added, and the solution was stirred for an additional 24 h. Hydrochloric acid (1 mL, 5% HCl solution in deionized water) was added, and the mixture was stirred for 30 min before the layers were allowed to settle. The aqueous layer was collected, and the water was evaporated under reduced pressure to yield an orange oil (0.232 g, 104%). The product was >95% pure by $^{31}$P NMR spectroscopy, and no significant impurities were visible in the $^1$H or $^{13}$C NMR spectra so the hydroxyl(tetra[ethyleneoxy])propylphosphonic acid was not purified further before use. It is likely that all of the water is not removed during evaporation because of the hydrophilic nature of the hydroxyl(tetra[ethyleneoxy])propylphosphonic acid.

$^1$H NMR (300 MHz, CD$_3$OD, δ): 3.70-3.52 (m, 18H), 1.93-1.75 (m, 4H). $^{13}$CNMR (125.7 MHz, CD$_3$OD, δ): 73.61, 71.88, 71.74, 71.62, 71.56, 71.42, 71.19, 62.29, 24.43 (d, J) 139 Hz), 24.13 (d, J)4 Hz). $^{31}$P NMR (121.6 MHz, CD$_3$OD, δ): 32.47. FTIR (neat): 3362, 2927, 2881, 1718, 1456, 1352, 1249, 1086, 946 cm$^{-1}$. LRMS (ESI): 315 (M−H)

Examples 5-6

Preparation of Octadecylphosphonic Acid and Undecylphosphonic Acid

The compound of Examples 2 and 3 were reacted as in Example 4 to obtain the title compounds.

Example 7

Yttria Nanoparticle Carbonate Removal by TFA

Yttria nanoparticles (35 mg Nanocerox) were dispersed by sonication in 20 mL acetonitrile and were transferred to a 50 mL round-bottomed flask. Trifluoroacetic acid (1.5 g) was added, and the reaction mixture was stirred overnight (15 h) at room temperature. Nano-particles were collected by centrifugation, and the solvent was removed under reduced pressure to give carbonate-free nanoparticles.

Examples 8-10

Figure 5:
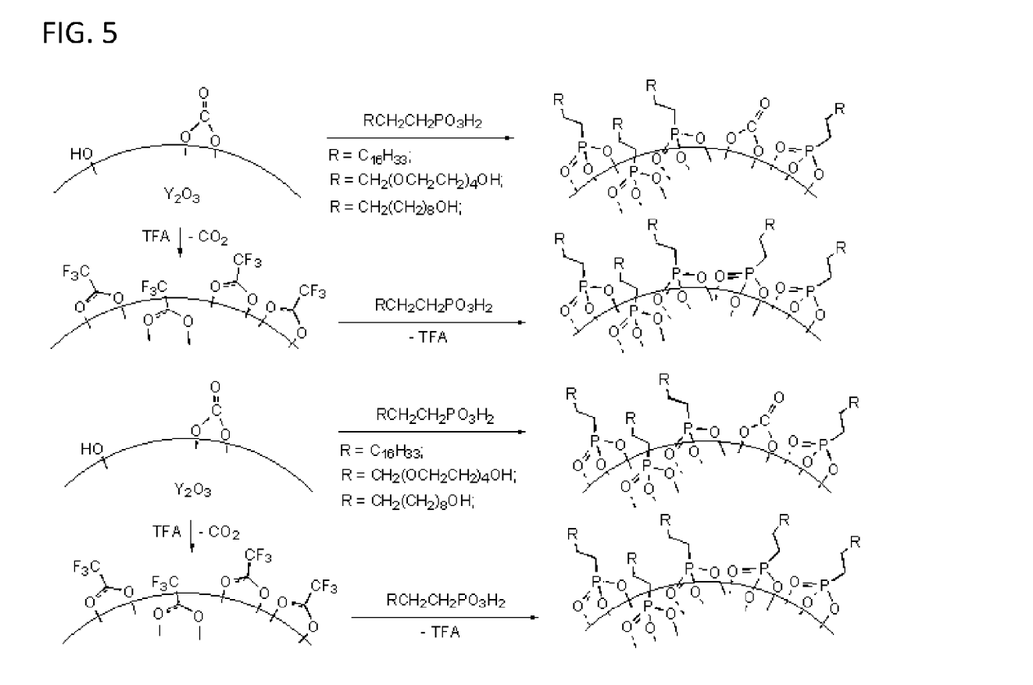
FIG. 5 depicts the surface modification of yttria particles by hydrophobic or hydrophilic phosphonates, or by phosphonates of intermediate hydrophilicity.

Phosphonate Coating of Nanoparticles (FIG. 5)

Nanoparticles (35 mg, as received or TFA-treated, Example 7) were dispersed by sonication in 10 mL of THF and were transferred to 50 mL round-bottomed flasks containing the phosphonic acids of Examples 4-6 ($2.3 \times 10^{-5}$ mol) in 25 mL of THF. The reaction mixtures were then stirred for 3 h at room temperature, and the nanoparticles were collected by centrifugation. In the case of coating with octadecylphosphonic acid, 10 mL of methanol was added to the THF suspension to help precipitate the particles on centrifugation. The phosphonate-coated nano-particles were washed by dispersing in 20 mL of methanol containing nine drops of 0.05 M NaOH-methanol solution. This suspension was manually shaken for 5 min, and the particles were collected by centrifugation to yield three sets of nanoparticles coated with the respective phosphonic acids of Examples 4-6.

Figure 2:
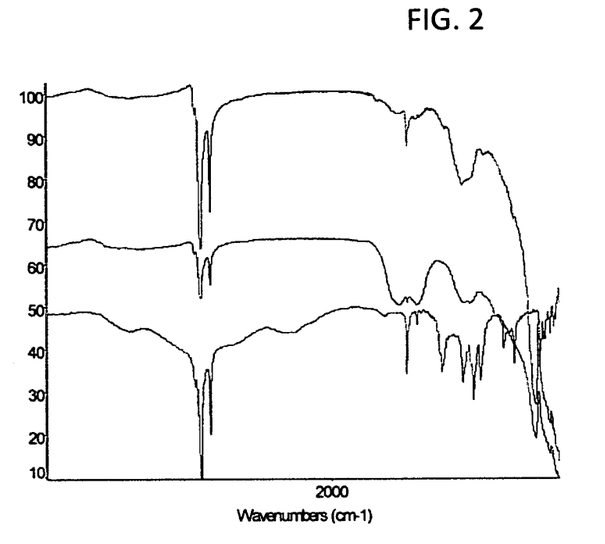
FIG. 2 depicts the IR spectrum of octadecylphosphonic acid (ODPA) (bottom), which was deposited on the $Y_2O_3$ particles of FIG. 1 to yield particles with the middle and top IR spectra respectively.

It was discovered that even in the presence of carbonate surface contaminants, simply stirring a suspension of $Y_2O_3$ nanoparticles in a tetrahydrofuran (THF) solution of octadecylphosphonic acid (ODPA; Example 8) gave, after isolation and rinsing, particles coated with a film of octadecylphosphonate. The IR spectrum (FIG. 2) had peaks ($CH_2$) 2919 and 2850 $cm^{-1}$ characteristic of ordered aliphatic chains. There was a broad band from 1160 to 990 $cm^{-1}$ and a sharp peak at 1090 $cm^{-1}$ attributed to P—O; there was no band at 1240 $cm^{-1}$ (P=O), which is consistent with a tridentate-bound phosphonate film. However, carbonate bands were still apparent.

Figure 1:
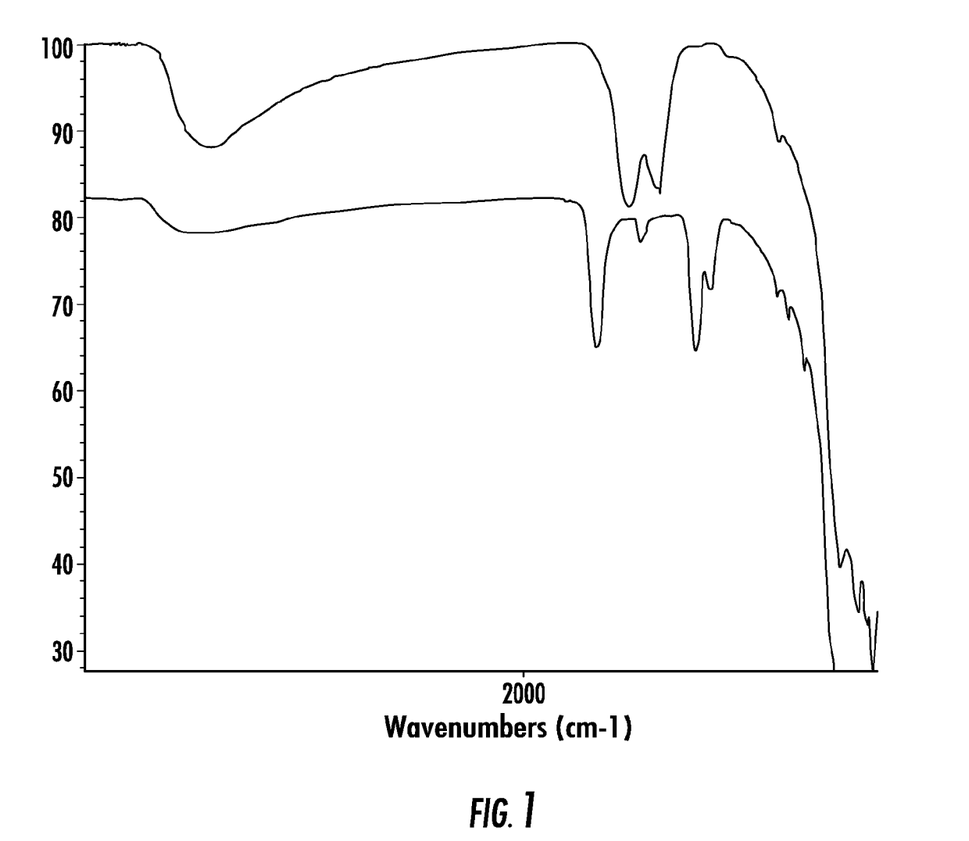
FIG. 1 depicts the IR spectrum of "as received" $Y_2O_3$ (top) showing strong carbonate bands that can be removed by TFA-treatment to yield particles with the bottom IR spectrum.

Example 7 demonstrates that surface carbonate can be removed from yttria by treating a suspension of the uncoated particles with trifluoroacetic acid (TFA) in acetonitrile. The resulting particle surfaces showed TFA coordination (RCOO—)1675, 1460 $cm^{-1}$; and C—F 1220 and 1160 $cm^{-1}$ (FIG. 1) and were more resistant than native yttria to reaction with atmospheric $CO_2$. It did react readily with a solution of the Example 2 compound after rinsing with methanolic NaOH, and the IR spectrum of these particles showed the trifluoroacetate bands to be absent and aliphatic and phosphonate regions to be similar to those for undecyl-phosphonate coated particles. TFA treatment, although useful in removing surface carbonate, has only a small effect on the formation of the deposited organic film As-received yttria nanoparticles do not suspend well in various organic solvents such as THF; they agglomerate even after sonication. SEM images of these particles show micrometer dimension aggregates of 40-80 nm crystallites. Dynamic light scattering (DLS) measurements of nanoparticles dispersed by sonication in THF show an average hydrodynamic diameter of approximately 420 nm. It is likely that sonication fractures the micrometer-dimension aggregates seen by SEM into the smaller ones measured by DLS.

ODPA-coated particles sonicated in THF showed DLS particle sizes of 296 and 466 nm, for TFA-treated particles, respectively. The difference in measured particle sizes may result from differences in their surface composition (surface carbonate and/or phosphonate) and solvents used in their preparation (untreated particles in THF; the treated particle precursor in acetonitrile before the coating reaction. Despite their relatively large sizes, the particles were easily suspended in nonaqueous media. Interestingly, gross suspendability characteristics did not depend on the presence of residual carbonate: both TFA-treated and non-TFA-treated particles showed suspendability that was good in $CHCl_3$ or $CH_2Cl_2$ and better in THF or ethyl acetate. Thus, whereas any remaining large aggregates quickly settled out, smaller particles remained suspended for weeks.

As-received yttria nanoparticles can however be suspended in water with sonication, but they begin to agglomerate and settle out of suspension after several hours. Because biological applications require better aqueous suspendability for these nanoparticles, a tetraethylene glycol-containing phosphonate was synthesized and bound to the yttria surface. First, tetraethylene glycol was monoallylated using allyl bromide and NaOH in refluxing THF and was then acetylated in $CH_2Cl_2$ at 0° C. using acetyl chloride and a tertiary amine to give the Example 1 starting material.

Figure 3:
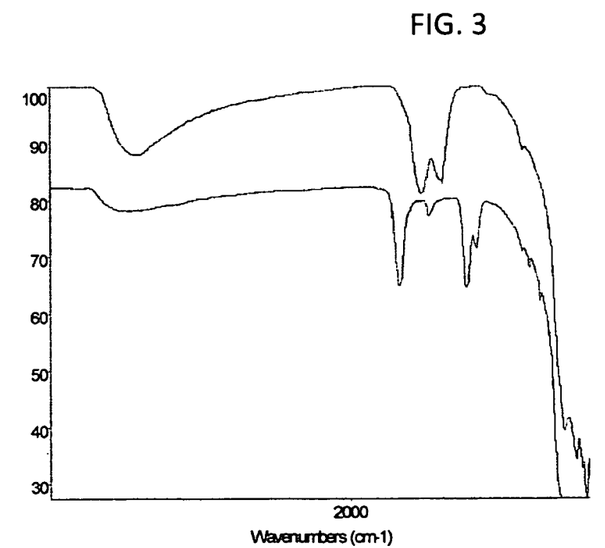
FIG. 3 depicts the IR spectrum of hydroxyl(tetra[ethyleneoxy])propylphosphonic acid, which was deposited on the $Y_2O_3$ particles of FIG. 1 to yield particles with the middle and top IR spectra respectively.

The dimethyl phosphonate ester derivative was then prepared as in Example 1 using 3:1 dimethyl phosphite to the starting material heated to 105° C. Radical initiator tert-butyl peroxybenzoate was then added; additional tert-butyl peroxybenzoate was added after 1 and 2 h of reaction. Chromatography on silica was adequate to purify the reaction product. $^{1}H$ NMR spectrum of consists of a series of complex multiplets at δ 1.95-1.78 for the methylene protons closest to the phosphorus ($^{1}J_{P-C}$ 141 Hz; $^{2}J_{P-C}$ 5 Hz) and a series of over-lapping AA'BB' patterns for the $CH_2$ groups of the ethyleneoxy units (δ 4.2 and 3.8-3.5). Phosphonate ester groups ($^{31}P$ NMR, $CDCl_3$, δ36.21) were cleaved Hydrolysis of the acetate with a stoichiometric amount of aqueous HCl gave hydroxy(tetra[ethyleneoxy])propylphosphonic acid ($^{31}P$ NMR, $CD_3OD$, δ 32.47). The phosphonic acid was deposited on yttria or TFA-treated yttria by stirring the particles for 3 h in a THF solution of the compound. Any impurities remaining from the preparation of non-TFA-treated particles were deemed to be removed by washing the particles. IR spectra of treated and non-treated coated particles were similar, with the exception of carbonate bands present in non-treated particles (FIG. 3). For both treated and non-treated particles, ($CH_2$) 2870 (br) and 2930 $cm^{-1}$ (shoulder) were observed, similar to disordered oligoethylene glycol chains of thiolate derivatives on gold. Similar to ODPA-coated particles, the band for P—O from 1200 to 960 $cm^{-1}$, the peak at 1110 $cm^{-1}$, and the absence of a peak near 1240 $cm^{-1}$ are consistent with tridentate phosphonate coordination.

After coating, treated and non-treated particles suspend readily in water with agitation. Sonication enables longer-term suspension. Smaller particles remain suspended for days, and unlike as-received particles that stay visibly aggregated after settling out, coated particles can be resuspended easily by manual agitation. Hydrodynamic diameters of as received particles in water were measured to be 300 nm, whereas those of coated particles that were treated with TFA and not treated with TFA were 238 and 400 nm, respectively. Here too, observed DLS size differences are likely derived from particle surface composition and the solvent employed in their preparation. Partitioning of coated particles both treated and not treated with TFA between $CHCl_3$ and water occurred as expected for the hydrophilicity of the phosphonate monolayer.

Mixing $CHCl_3$ and hydrophilic particles coated with hydroxy(tetra[ethylene-oxy])propylphosphonic acid, followed by the addition of water and agitation gave an aqueous suspension of nanoparticles above the organic layer, regardless of whether or not the particles had been treated with TFA. Conversely, mixing water and hydrophobic particles coated with ODPA gave particles floating on the water surface until $CHCl_3$ was added and the mixture was sonicated, again regardless of whether or not the particles had been treated with TFA. The biphasic mixture was then a suspension of TFA treated particles or particles that had not been treated with TFA in the organic layer only.

A third system was examined in which yttria nanoparticles were bonded to 11-hydroxyundecylphosphonic acid, which was previously used to attach biomolecules to solid metal oxide surfaces. The resulting particles have hydrophilicity intermediate between that of particles coated with hydroxy(tetra[ethyleneoxy])propylphosphonic acid and ODPA-coated particles. IR spectra are characteristic of less-well-ordered films with ($CH_2$) 2923 and 2852 $cm^{-1}$ for particles used "as received" and 2921 and 2851 $cm^{-1}$ for TFA-treated particles. The phosphonate regions for both "as received" and TFA-treated particles showed P—O as a broad band centered at 1060 $cm^{-1}$, similar to those for ODPA-coated particles and particles coated with hydroxy(tetra[ethyleneoxy])propylphosphonic acid.

The foregoing examples demonstrate that phosphonates readily bond to yttrium oxide nanoparticle surfaces and that the hydrophilic characteristics of these particles can be controlled by choice of the phosphonic acid. This is unexpected because one would ordinarily expect the basic metal oxide particles to be dissolved by these acids. Bonding occurs at room temperature, which contrasts with the reactivity of phosphonic acids with particles of several other metal oxides. For example, alkylphosphonic acids have been used to surface modify iron oxide nanoparticles, but this requires elevated temperature, long reaction times, and or high-energy ultrasound treatment. Ordinarily, phosphonic acid reactivity correlates with the basicity of the metal oxide substrate; for example, $Al_2O_3$ and $ZrO_2$ show higher reactivity toward them than does $TiO_2$. The ease with which yttria reacts with ambient $CO_2$ suggests a surface of high basicity; however, unlike $Al_2O_3$, which is also highly reactive with phosphonic acids and gives phosphonate salts, yttria yields a stable organic film.

Although the present invention has been described in considerable detail with reference to certain versions thereof, other versions are possible. Therefore, the spirit and scope of the appended claims should not be limited to the description of the versions contained herein.

What is claimed is:

1. Particles comprising oxide, oxysulfide, or phosphate host particles with a self-assembled monolayer consisting of organophosphonate ligands covalently bonded thereto, wherein said host particles comprise ions of one or more rare earth elements, wherein said covalent bonding to the host particle surfaces is via tridentate phosphonate coordination, wherein said particles are less than about 100 microns in size, and wherein said organophosphonate ligands are of formula:

R—P(=O)(—OH)$_2$ wherein R is selected from the group consisting of linear alkyl, branched alkyl, linear alkylenyl, and branched alkylenyl moieties having from about two to about 40 carbon atoms, 0 to about 20 heteroatoms selected independently from oxygen and nitrogen, and omega-functionalized organic moieties, and wherein a photosensitizer compound or one or more biomolecular probes are covalently attached via said omega-functionalized organic moieties.

2. The particles of claim 1, wherein the rare earth element ions are ions of one or more rare earth elements selected from the group consisting of strontium, europium, cerium, terbium, dysprosium, holmium, erbium, thulium, ytterbium and lutetium.

3. The particles of claim 2, wherein said rare earth element ions comprise a combination of ytterbium ions and one or more ions selected from the group consisting of erbium, holmium and thulium ions.

4. The particles of claim 1, wherein said host particles comprise oxides or oxysulfides of one or more elements selected from the group consisting of lanthanum, yttrium, lead, zinc, cadmium, beryllium, magnesium, calcium, strontium, barium, aluminum, radium, silicon and germanium.

5. The particles of claim 1, wherein said host particles comprise oxides or oxysulfides of one or more Group II-IV semiconductor compounds.

6. The particles of claim 1, wherein said host particles comprise one or more compounds selected from the group consisting of yttrium oxide ($Y_2O_3$), lanthanum oxysulfide ($La_2O_2S$), yttrium oxysulfide ($Y_2O_2S$), calcium tungstate ($CaWO_4$) and gadolinium oxysulfide ($Gd_2O_2S$).

7. The particles of claim 6, wherein said host particles comprise one or more compounds selected from the group consisting of yttrium oxide doped with erbium ions ($Y_2O_3$:Er), and yttrium oxide doped with ytterbium ions ($Y_2O_3$:Yb).

8. The particles of claim 1, wherein the R groups of said organophosphonate ligands comprise poly(alkylene oxide) moieties.

9. The particles of claim 8, wherein said poly(alkylene oxide) moieties comprise tetraethylene glycols with omega-functionalized organic moieties.

10. The particles of claim 1, wherein the R groups of said organophosphonate ligands comprise butyl, hexyl, octyl, dodecyl, octadecyl, or undecyl moieties.

11. The particles of claim 1, wherein said monolayer is more hydrophilic than the native surface of the underlying host particles.

12. A stable liquid suspension comprising the coated particles of claim 11 dispersed in a polar solvent.

13. A stable liquid suspension comprising a dispersion in a non-polar solvent of the particles of claim 11 encapsulated in micelles capable of suspending hydrophilic particles in a non-polar solvent or in cyclodextrins or liposomes with hydrophilic cores and hydrophobic exteriors.

14. The particles of claim 1, wherein said monolayer is more hydrophobic than the native surface of the underlying host particles.

15. A stable liquid suspension comprising the particles of claim 14 dispersed in a non-polar solvent.

16. A stable liquid suspension comprising a dispersion in a polar solvent of the particles of claim 14 encapsulated in micelles capable of suspending hydrophobic particles in a polar solvent or in cyclodextrins or liposomes with hydrophobic cores and hydrophilic exteriors.

17. The particles of claim 1, wherein said biomolecular probes are selected from the group consisting of proteins and peptides that bind to biological markers.

18. The particles of claim 17, wherein said proteins are selected from the group consisting of avidin and antibodies.

19. The particles of claim 1, wherein a photosensitizer compound is covalently attached via said omega-functionalized organic moieties.

20. The particles of claim 1, wherein said particles are mono-disperse and have a particle size less than 1 micron.

21. The particles of claim 20, wherein said particles have a particle size less than 100 nanometers.

* * * * *